United States Patent
Zhang et al.

(10) Patent No.: US 8,496,677 B2
(45) Date of Patent: Jul. 30, 2013

(54) METHODS AND DEVICES FOR CUTTING TISSUE

(75) Inventors: Zhiyong Zhang, Edina, MN (US); Hussain S. Rangwala, Orange, CA (US); Robert Wayne VanPelt, Jr., Saint Paul, MN (US); Ethan Andrew Guggenheimer, Minneapolis, MN (US); William Joseph Whealon, Chaska, MN (US); John Robert Moberg, Elk River, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/958,488

(22) Filed: Dec. 2, 2010

(65) Prior Publication Data

US 2011/0130777 A1    Jun. 2, 2011

Related U.S. Application Data

(60) Provisional application No. 61/265,863, filed on Dec. 2, 2009.

(51) Int. Cl.
*A61B 17/22* (2006.01)
(52) U.S. Cl.
USPC .................................................. 606/159
(58) Field of Classification Search
USPC ............. 606/158, 159, 167, 170, 171, 180, 606/198; 604/22
See application file for complete search history.

(56) References Cited

U.S. PATENT DOCUMENTS

| | | | |
|---|---|---|---|
| 1,481,078 | A | 1/1924 | Albertson |
| 2,178,790 | A | 11/1939 | Henry |
| 2,701,559 | A | 2/1955 | Cooper |
| 2,850,007 | A | 9/1958 | Lingley |
| 3,064,651 | A | 11/1960 | Henderson |
| 3,082,805 | A | 3/1963 | Royce |
| 3,320,957 | A | 5/1967 | Sokolik |
| 3,614,953 | A | 10/1971 | Moss |
| 3,683,891 | A | 8/1972 | Eskridge et al. |
| 3,705,577 | A | 12/1972 | Sierra |
| 3,732,858 | A | 5/1973 | Banko |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

May 25, 2011 PCT International Search Report and Written Opinion for corresponding PCT Application No. PCT/US2010/058654 (15 pages).

(Continued)

*Primary Examiner* — Tuan V Nguyen
(74) *Attorney, Agent, or Firm* — Alana T. Bergman, Esq.

(57) ABSTRACT

A catheter which includes a cutting element having one or more raised elements is provided. The cutting element has a cup-shaped surface at the distal end that may be smooth and continuous except for the raised elements. The raised elements have a surface that tends to direct cut particles of material towards one or more of the axis of rotation of the cutting element, the catheter axis, or a particle collection chamber. In further aspects of the invention, a cutting element oscillates in a direction roughly parallel to the axis of rotation of the cutting element.

24 Claims, 13 Drawing Sheets

U.S. PATENT DOCUMENTS

| | | |
|---|---|---|
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A * | 3/1988 | Henrie .............................. 604/22 |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A * | 6/1988 | Kensey et al. ................... 604/22 |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |

| | | | | | |
|---|---|---|---|---|---|
| 5,250,059 A | 10/1993 | Andreas et al. | 5,507,760 A | 4/1996 | Wynne et al. |
| 5,250,065 A | 10/1993 | Clement et al. | 5,507,761 A | 4/1996 | Duer |
| 5,263,928 A | 11/1993 | Trauthen et al. | 5,507,795 A | 4/1996 | Chiang et al. |
| 5,263,959 A | 11/1993 | Fischell | 5,512,044 A | 4/1996 | Duer |
| 5,267,955 A | 12/1993 | Hanson | 5,514,115 A | 5/1996 | Frantzen et al. |
| 5,267,982 A | 12/1993 | Sylvanowicz | 5,520,189 A | 5/1996 | Malinowski et al. |
| 5,269,793 A | 12/1993 | Simpson et al. | 5,522,825 A | 6/1996 | Kropf et al. |
| 5,273,526 A | 12/1993 | Dance et al. | 5,522,880 A | 6/1996 | Barone et al. |
| 5,282,484 A | 2/1994 | Reger | 5,527,292 A | 6/1996 | Adams et al. |
| 5,284,486 A | 2/1994 | Kotula et al. | 5,527,298 A | 6/1996 | Vance et al. |
| 5,285,795 A | 2/1994 | Ryan et al. | 5,527,325 A | 6/1996 | Conley et al. |
| 5,295,493 A | 3/1994 | Radisch, Jr. | 5,531,685 A | 7/1996 | Hemmer et al. |
| 5,300,085 A | 4/1994 | Yock | 5,531,690 A | 7/1996 | Solar |
| 5,306,294 A | 4/1994 | Winston et al. | 5,531,700 A | 7/1996 | Moore et al. |
| 5,308,354 A | 5/1994 | Zacca et al. | 5,540,707 A | 7/1996 | Ressemann et al. |
| 5,312,425 A | 5/1994 | Evans et al. | 5,549,601 A | 8/1996 | McIntyre et al. |
| 5,312,427 A | 5/1994 | Shturman | 5,554,163 A | 9/1996 | Shturman |
| 5,314,438 A | 5/1994 | Shturman | 5,556,408 A | 9/1996 | Farhat |
| 5,318,032 A | 6/1994 | Lonsbury et al. | 5,558,093 A | 9/1996 | Pomeranz |
| 5,318,528 A | 6/1994 | Heaven et al. | 5,562,726 A | 10/1996 | Chuter |
| 5,318,576 A | 6/1994 | Plassche, Jr. et al. | 5,562,728 A | 10/1996 | Lazarus et al. |
| 5,321,501 A | 6/1994 | Swanson et al. | 5,569,275 A | 10/1996 | Kotula et al. |
| 5,322,508 A | 6/1994 | Viera | 5,569,276 A | 10/1996 | Jang et al. |
| 5,350,390 A | 9/1994 | Sher | 5,569,277 A | 10/1996 | Evans et al. |
| 5,356,418 A | 10/1994 | Shturman | 5,569,279 A | 10/1996 | Rainin |
| 5,358,472 A | 10/1994 | Vance et al. | 5,570,693 A | 11/1996 | Jang et al. |
| 5,358,485 A | 10/1994 | Vance et al. | 5,571,122 A | 11/1996 | Kelly et al. |
| 5,360,432 A | 11/1994 | Shturman | 5,571,130 A | 11/1996 | Simpson et al. |
| 5,366,463 A | 11/1994 | Ryan | 5,575,817 A | 11/1996 | Martin |
| 5,368,035 A | 11/1994 | Hamm et al. | 5,584,842 A | 12/1996 | Fogarty et al. |
| 5,370,609 A | 12/1994 | Drasler et al. | 5,584,843 A | 12/1996 | Wulfman et al. |
| 5,370,651 A | 12/1994 | Summers | 5,609,605 A | 3/1997 | Marshall et al. |
| 5,372,601 A | 12/1994 | Lary | 5,618,293 A | 4/1997 | Sample et al. |
| 5,372,602 A | 12/1994 | Burke | 5,620,447 A | 4/1997 | Smith et al. |
| 5,373,619 A | 12/1994 | Fleischhacker et al. | 5,624,457 A | 4/1997 | Farley et al. |
| 5,373,849 A | 12/1994 | Maroney et al. | 5,626,562 A | 5/1997 | Castro |
| 5,377,682 A | 1/1995 | Ueno et al. | 5,626,576 A | 5/1997 | Janssen |
| 5,378,234 A | 1/1995 | Hammerslag et al. | 5,628,761 A | 5/1997 | Rizik |
| 5,383,460 A | 1/1995 | Jang et al. | 5,632,754 A | 5/1997 | Farley et al. |
| 5,395,311 A | 3/1995 | Andrews | 5,632,755 A | 5/1997 | Nordgren et al. |
| 5,395,313 A | 3/1995 | Naves et al. | 5,634,464 A | 6/1997 | Jang et al. |
| 5,395,335 A | 3/1995 | Jang | 5,643,296 A | 7/1997 | Hundertmark et al. |
| 5,397,345 A | 3/1995 | Lazarus | 5,643,298 A | 7/1997 | Nordgren et al. |
| 5,402,790 A | 4/1995 | Jang et al. | 5,649,941 A | 7/1997 | Lary |
| 5,403,334 A | 4/1995 | Evans et al. | 5,660,180 A | 8/1997 | Malinowski et al. |
| 5,409,454 A | 4/1995 | Fischell et al. | 5,662,671 A | 9/1997 | Barbut et al. |
| 5,413,107 A | 5/1995 | Oakley et al. | 5,665,098 A | 9/1997 | Kelly et al. |
| 5,419,774 A | 5/1995 | Willard et al. | 5,669,920 A | 9/1997 | Conley et al. |
| 5,423,740 A | 6/1995 | Sullivan | 5,674,232 A | 10/1997 | Halliburton |
| 5,423,799 A | 6/1995 | Shiu | 5,676,696 A | 10/1997 | Marcade |
| 5,423,838 A | 6/1995 | Willard | 5,676,697 A | 10/1997 | McDonald |
| 5,423,846 A | 6/1995 | Fischell | 5,681,336 A | 10/1997 | Clement et al. |
| 5,427,107 A | 6/1995 | Milo et al. | 5,682,897 A | 11/1997 | Pomeranz |
| 5,429,136 A | 7/1995 | Milo et al. | 5,683,449 A | 11/1997 | Marcade |
| 5,431,673 A | 7/1995 | Summers et al. | 5,683,453 A | 11/1997 | Palmaz |
| 5,441,510 A | 8/1995 | Simpson et al. | 5,688,234 A | 11/1997 | Frisbie |
| 5,443,446 A | 8/1995 | Shturman | 5,695,506 A | 12/1997 | Pike |
| 5,443,497 A | 8/1995 | Venbrux | 5,695,507 A | 12/1997 | Auth et al. |
| 5,444,078 A | 8/1995 | Yu et al. | 5,697,944 A | 12/1997 | Lary |
| 5,445,155 A | 8/1995 | Sieben | 5,700,240 A | 12/1997 | Barwick, Jr. et al. |
| 5,449,369 A | 9/1995 | Imran | 5,700,687 A | 12/1997 | Finn |
| 5,451,233 A | 9/1995 | Yock | 5,707,350 A | 1/1998 | Krause et al. |
| 5,454,809 A | 10/1995 | Janssen | 5,707,376 A | 1/1998 | Kavteladze et al. |
| 5,456,667 A | 10/1995 | Ham et al. | 5,707,383 A | 1/1998 | Bays et al. |
| 5,456,689 A | 10/1995 | Kresch et al. | 5,709,698 A | 1/1998 | Adams et al. |
| 5,458,585 A | 10/1995 | Salmon et al. | 5,713,913 A | 2/1998 | Lary et al. |
| 5,459,570 A | 10/1995 | Swanson et al. | 5,715,825 A | 2/1998 | Crowley |
| 5,464,016 A | 11/1995 | Nicholas et al. | 5,716,410 A | 2/1998 | Wang et al. |
| 5,470,415 A | 11/1995 | Perkins et al. | 5,720,735 A | 2/1998 | Dorros |
| 5,485,042 A | 1/1996 | Burke et al. | 5,724,977 A | 3/1998 | Yock et al. |
| 5,485,840 A | 1/1996 | Bauman | 5,728,123 A | 3/1998 | Lemelson et al. |
| 5,487,729 A | 1/1996 | Avellanet et al. | 5,733,296 A | 3/1998 | Rogers et al. |
| 5,489,295 A | 2/1996 | Piplani et al. | 5,735,816 A | 4/1998 | Lieber et al. |
| 5,491,524 A | 2/1996 | Hellmuth et al. | 5,741,270 A | 4/1998 | Hansen et al. |
| 5,496,267 A | 3/1996 | Drasler et al. | 5,766,192 A | 6/1998 | Zacca |
| 5,501,694 A | 3/1996 | Ressemann et al. | 5,772,674 A | 6/1998 | Nakhjavan |
| 5,503,155 A | 4/1996 | Salmon et al. | 5,775,327 A | 7/1998 | Randolph et al. |
| 5,505,210 A | 4/1996 | Clement | 5,776,114 A | 7/1998 | Frantzen et al. |
| 5,507,292 A | 4/1996 | Jang et al. | 5,776,153 A | 7/1998 | Rees |

| | | | | | | |
|---|---|---|---|---|---|---|
| 5,779,643 | A | 7/1998 | Lum et al. | 6,110,121 A | 8/2000 | Lenker |
| 5,779,673 | A | 7/1998 | Roth et al. | 6,120,515 A | 9/2000 | Rogers et al. |
| 5,779,721 | A | 7/1998 | Nash | 6,120,516 A | 9/2000 | Selmon et al. |
| 5,779,722 | A | 7/1998 | Shturman et al. | 6,126,649 A | 10/2000 | VanTassel et al. |
| 5,792,157 | A | 8/1998 | Mische et al. | 6,129,734 A | 10/2000 | Shturman et al. |
| 5,797,949 | A | 8/1998 | Parodi | 6,134,003 A | 10/2000 | Tearney et al. |
| 5,799,655 | A | 9/1998 | Jang et al. | 6,152,909 A | 11/2000 | Bagaoisan et al. |
| 5,807,329 | A | 9/1998 | Gelman | 6,152,938 A | 11/2000 | Curry |
| 5,810,867 | A | 9/1998 | Zarbatany et al. | 6,156,046 A | 12/2000 | Passafaro et al. |
| 5,816,923 | A | 10/1998 | Milo et al. | 6,157,852 A | 12/2000 | Selmon et al. |
| 5,820,592 | A | 10/1998 | Hammerslag | 6,159,195 A | 12/2000 | Ha et al. |
| 5,823,971 | A | 10/1998 | Robinson et al. | 6,159,225 A | 12/2000 | Makower |
| 5,824,039 | A | 10/1998 | Piplani et al. | 6,165,127 A | 12/2000 | Crowley |
| 5,824,055 | A | 10/1998 | Spiridigliozzi et al. | 6,179,859 B1 | 1/2001 | Bates et al. |
| 5,827,201 | A | 10/1998 | Samson et al. | 6,183,432 B1 | 2/2001 | Milo |
| 5,827,229 | A | 10/1998 | Auth et al. | 6,187,025 B1 | 2/2001 | Machek |
| 5,827,304 | A | 10/1998 | Hart | 6,190,353 B1 | 2/2001 | Makower et al. |
| 5,827,322 | A | 10/1998 | Williams | 6,191,862 B1 | 2/2001 | Swanson et al. |
| 5,830,224 | A | 11/1998 | Cohn et al. | 6,193,676 B1 | 2/2001 | Winston et al. |
| 5,836,957 | A | 11/1998 | Schulz et al. | 6,196,963 B1 | 3/2001 | Williams |
| 5,843,022 | A | 12/1998 | Willard et al. | 6,206,898 B1 | 3/2001 | Honeycutt et al. |
| 5,843,103 | A | 12/1998 | Wulfman | 6,217,527 B1 | 4/2001 | Selmon et al. |
| 5,843,161 | A | 12/1998 | Solovay | 6,217,549 B1 | 4/2001 | Selmon et al. |
| 5,855,563 | A | 1/1999 | Kaplan et al. | 6,217,595 B1 | 4/2001 | Shturman et al. |
| 5,865,748 | A | 2/1999 | Co et al. | 6,221,049 B1 | 4/2001 | Selmon et al. |
| 5,868,685 | A | 2/1999 | Powell et al. | 6,221,332 B1 | 4/2001 | Thumm et al. |
| 5,868,767 | A | 2/1999 | Farley et al. | 6,228,049 B1 | 5/2001 | Schroeder et al. |
| 5,871,536 | A | 2/1999 | Lazarus | 6,228,076 B1 | 5/2001 | Winston et al. |
| 5,873,882 | A | 2/1999 | Straub et al. | 6,231,546 B1 | 5/2001 | Milo et al. |
| 5,876,414 | A | 3/1999 | Straub | 6,231,549 B1 | 5/2001 | Noecker et al. |
| 5,879,397 | A | 3/1999 | Kalberer et al. | 6,235,000 B1 | 5/2001 | Milo et al. |
| 5,883,458 | A | 3/1999 | Sumita et al. | 6,238,405 B1 | 5/2001 | Findlay, III et al. |
| 5,888,201 | A | 3/1999 | Stinson et al. | 6,241,667 B1 | 6/2001 | Vetter et al. |
| 5,895,399 | A | 4/1999 | Barbut et al. | 6,241,744 B1 | 6/2001 | Imran et al. |
| 5,895,402 | A | 4/1999 | Hundertmark et al. | 6,245,012 B1 | 6/2001 | Kleshinski |
| 5,902,245 | A | 5/1999 | Yock | 6,258,052 B1 | 7/2001 | Milo |
| 5,910,150 | A | 6/1999 | Saadat | 6,263,236 B1 | 7/2001 | Kasinkas et al. |
| 5,911,734 | A | 6/1999 | Tsugita et al. | 6,264,611 B1 | 7/2001 | Ishikawa et al. |
| 5,916,210 | A | 6/1999 | Winston | 6,266,550 B1 | 7/2001 | Selmon et al. |
| 5,922,003 | A | 7/1999 | Anctil et al. | 6,277,138 B1 | 8/2001 | Levinson et al. |
| 5,935,108 | A | 8/1999 | Katoh et al. | 6,283,951 B1 | 9/2001 | Flaherty et al. |
| 5,938,645 | A | 8/1999 | Gordon | 6,283,983 B1 | 9/2001 | Makower et al. |
| 5,938,671 | A | 8/1999 | Katoh et al. | 6,299,622 B1 | 10/2001 | Snow et al. |
| 5,938,672 | A | 8/1999 | Nash | 6,299,623 B1 | 10/2001 | Wulfman |
| 5,941,869 | A | 8/1999 | Patterson et al. | 6,302,875 B1 | 10/2001 | Makower et al. |
| 5,947,985 | A | 9/1999 | Imran | 6,305,834 B1 | 10/2001 | Schubert et al. |
| 5,948,184 | A | 9/1999 | Frantzen et al. | 6,312,444 B1 | 11/2001 | Barbut |
| 5,951,480 | A | 9/1999 | White et al. | 6,319,242 B1 | 11/2001 | Patterson et al. |
| 5,951,482 | A | 9/1999 | Winston et al. | 6,319,275 B1 | 11/2001 | Lashinski et al. |
| 5,954,745 | A | 9/1999 | Gertler et al. | 6,330,884 B1 | 12/2001 | Kim |
| 5,968,064 | A | 10/1999 | Selmon et al. | 6,355,005 B1 | 3/2002 | Powell et al. |
| 5,972,019 | A | 10/1999 | Engelson et al. | 6,361,545 B1 | 3/2002 | Macoviak et al. |
| 5,985,397 | A | 11/1999 | Witt et al. | 6,375,615 B1 | 4/2002 | Flaherty et al. |
| 5,989,281 | A | 11/1999 | Barbut et al. | 6,383,195 B1 | 5/2002 | Richard |
| 5,997,557 | A | 12/1999 | Barbut et al. | 6,383,205 B1 | 5/2002 | Samson et al. |
| 6,001,112 | A | 12/1999 | Taylor | 6,394,976 B1 | 5/2002 | Winston et al. |
| 6,010,449 | A | 1/2000 | Selmon et al. | 6,398,798 B2 | 6/2002 | Selmon et al. |
| 6,010,522 | A | 1/2000 | Barbut et al. | 6,422,736 B1 | 7/2002 | Antoniades et al. |
| 6,013,072 | A | 1/2000 | Winston et al. | 6,423,081 B1 | 7/2002 | Lee et al. |
| 6,019,778 | A | 2/2000 | Wislon et al. | 6,425,870 B1 | 7/2002 | Flesch |
| 6,022,362 | A | 2/2000 | Lee et al. | 6,428,551 B1 | 8/2002 | Hall et al. |
| 6,027,450 | A | 2/2000 | Brown et al. | 6,428,552 B1 | 8/2002 | Sparks |
| 6,027,460 | A | 2/2000 | Shturman | 6,443,966 B1 | 9/2002 | Shiu |
| 6,027,514 | A | 2/2000 | Stine et al. | 6,445,939 B1 | 9/2002 | Swanson et al. |
| 6,032,673 | A | 3/2000 | Savage et al. | 6,447,525 B2 | 9/2002 | Follmer et al. |
| 6,036,646 | A | 3/2000 | Barthe et al. | 6,451,036 B1 | 9/2002 | Heitzmann et al. |
| 6,036,656 | A | 3/2000 | Slater | 6,454,779 B1 | 9/2002 | Taylor |
| 6,036,707 | A | 3/2000 | Spaulding | 6,475,226 B1 | 11/2002 | Belef et al. |
| 6,048,349 | A | 4/2000 | Winston et al. | 6,482,217 B1 | 11/2002 | Pintor et al. |
| 6,050,949 | A | 4/2000 | White et al. | 6,497,711 B1 | 12/2002 | Plaia et al. |
| 6,063,093 | A | 5/2000 | Winston et al. | 6,501,551 B1 | 12/2002 | Tearney et al. |
| 6,066,153 | A | 5/2000 | Lev | 6,520,975 B2 | 2/2003 | Branco |
| 6,068,603 | A | 5/2000 | Suzuki | RE38,018 E | 3/2003 | Anctil et al. |
| 6,068,638 | A | 5/2000 | Makower | 6,532,380 B1 | 3/2003 | Close et al. |
| 6,081,738 | A | 6/2000 | Hinohara et al. | 6,533,749 B1 | 3/2003 | Mitusina et al. |
| RE36,764 | E | 7/2000 | Zacca et al. | 6,561,998 B1 | 5/2003 | Roth et al. |
| 6,095,990 | A | 8/2000 | Parodi | 6,565,588 B1 | 5/2003 | Clement et al. |
| 6,099,542 | A | 8/2000 | Cohn et al. | 6,569,177 B1 | 5/2003 | Dillard et al. |
| 6,106,515 | A | 8/2000 | Winston et al. | 6,592,526 B1 | 7/2003 | Lenker |

| | | |
|---|---|---|
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |

| | | | |
|---|---|---|---|
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 93/16642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | WO 2006/058223 A2 | 6/2006 |
| WO | WO 2006/066012 A2 | 6/2006 |

OTHER PUBLICATIONS

Abstract of DE 44 44 166 Al (1 page).
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).
Mar. 29, 2011 PCT Invitation to Pay Additional Fees and Partial Search Report for corresponding PCT Application No. PCT/US2010/058654 (8 pages).
Abstract of JP2206452A (1 page).
Amplatz Coronary Catheters, posted: Feb. 25, 2009, [online], [retrieved on Mar. 29, 2011], retrieved from the Cardiophile MD website using Internet <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiophile MD website using Internet <URL:http://cardiophile.org/2009/02/judkins-left-coronary-catheter.html> (3 pages).
Jul. 19, 2011 Communication in European Application No. 04760155.4 (5 pages).
Jan. 18, 2012 PCT International Search Report and Written Opinion in Application No. PCT/US2011/058107 (19 pages).
Translation of Aug. 15, 2007 mailed Japanese Patent Office Action, Application No. 1999-139033 (4 pages).

\* cited by examiner

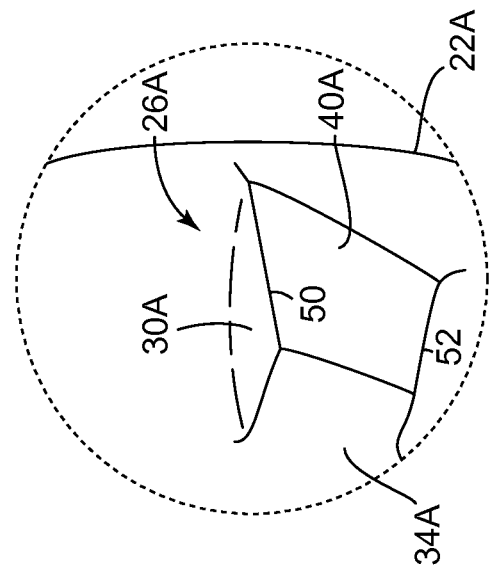
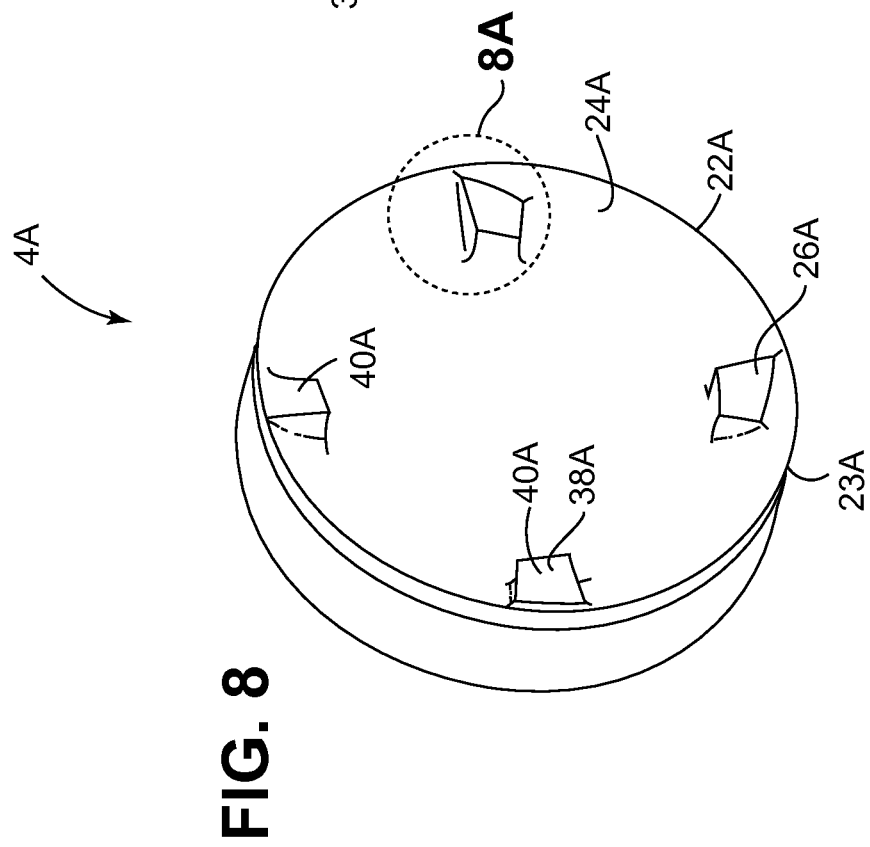

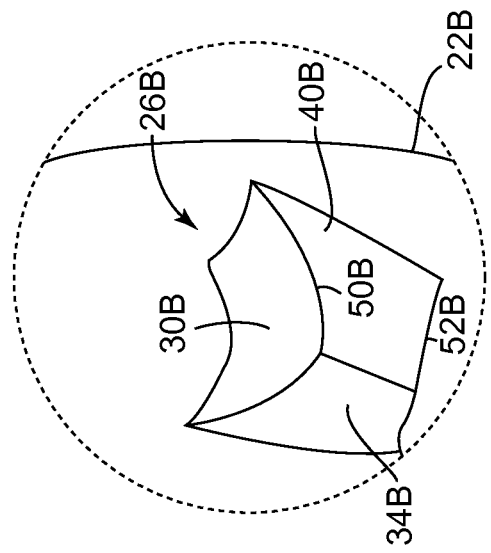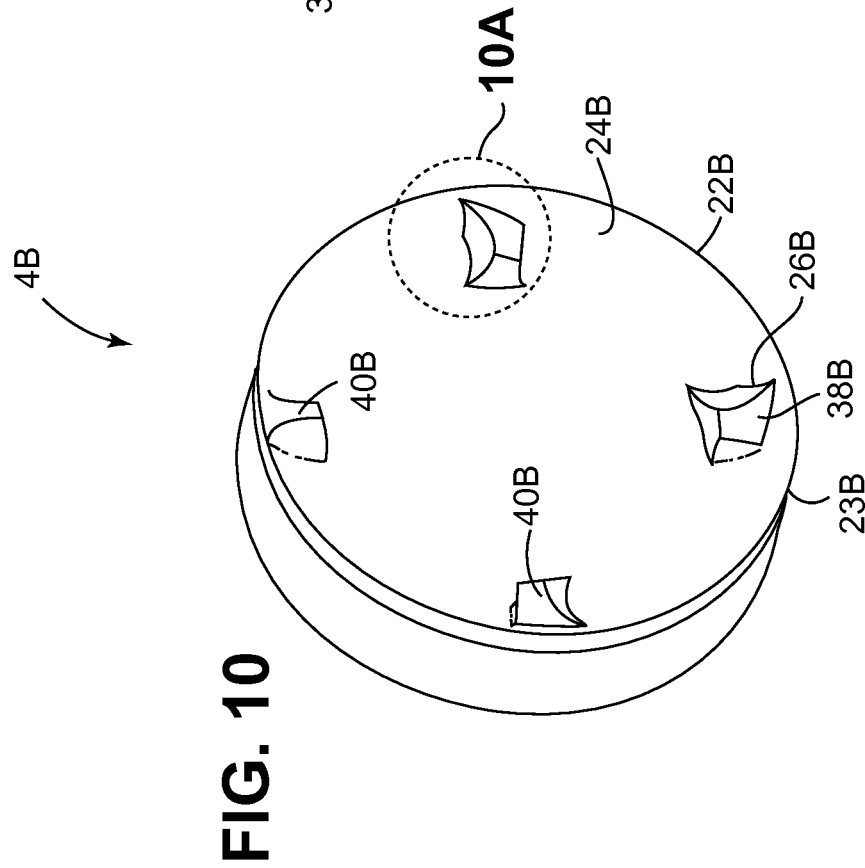

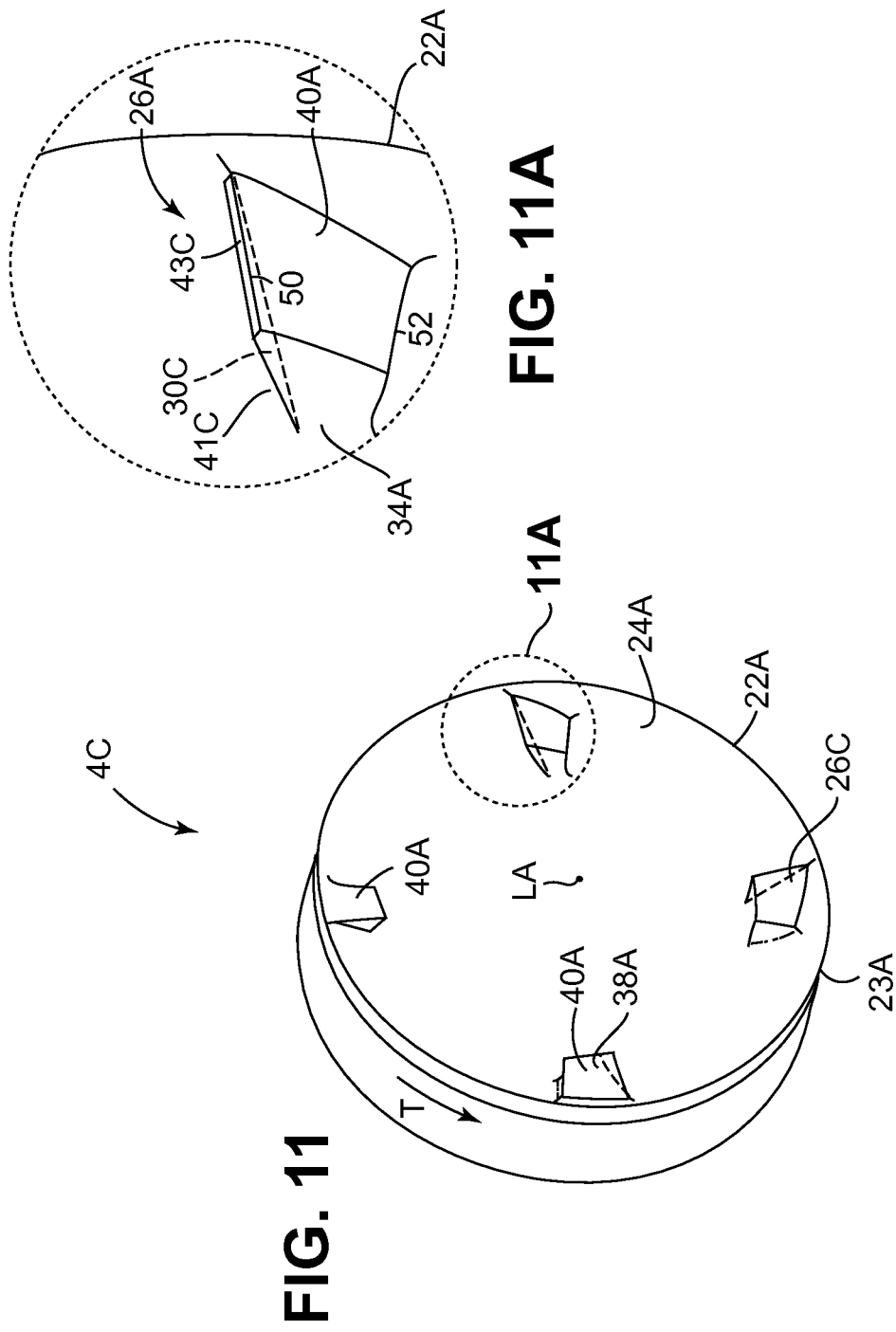

METHODS AND DEVICES FOR CUTTING TISSUE

This application claims the benefit of U.S. Provisional Patent Application No. 61/265,863, filed Dec. 2, 2009, entitled "Methods and Devices for Cutting Tissue", the contents of which are hereby incorporated by reference herein.

FIELD OF THE INVENTION

The present invention is directed to cutting elements for an atherectomy catheter and methods of cutting material from a blood flow lumen using a rotating cutting element.

BACKGROUND OF THE INVENTION

Catheters are used to remove unwanted tissue from the body. Atherectomy catheters are used to remove material from a blood vessel to open the blood vessel and improve blood flow through the vessel.

One problem that occurs when removing material from a blood vessel is that the material may be either soft or hard and may vary during the cutting process. As such, the cutting element should be able to cut both hard tissue and soft tissue. Another problem that occurs when using a rotating cutter is that particles of material tend to be displaced in a direction tangential to the cutter, away from the catheter and away from catheter based particle collection structures. It is therefore also desirable to direct cut particles towards the catheter, and especially towards a catheter based particle collection structure.

SUMMARY OF THE INVENTION

The invention provides an atherectomy catheter comprising: a body having an opening; a rotatable shaft coupled to the body; a tissue collection chamber coupled to the body and positioned distal to the cutting element; a cutting element coupled to the rotatable shaft for rotating the cutting element about an axis of rotation, the cutting element having a cup-shaped surface and a cutting edge, the cup-shaped surface being configured to re-direct tissue cut by the cutting edge in a distal direction when the cup-shaped surface moves in the distal direction; and a raised element extending outwardly from the cup-shaped surface of the cutting element, the raised element being configured to direct cut particles of material towards one of more of the axis of rotation of the cutting element, a catheter longitudinal axis, or the tissue collection chamber.

The invention provides an atherectomy catheter comprising: a body having an opening; a rotatable shaft coupled to the body; a tissue collection chamber coupled to the body and positioned distal to the cutting element; and a cutting element coupled to the rotatable shaft for rotating the cutting element about an axis of rotation, the cutting element having a cutting edge, and the cutting element being configured to oscillate in a direction substantially parallel to the axis of rotation of the cutting element.

The invention provides a method of removing material from a body lumen, the method comprising providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft for rotating the cutting element about an axis of rotation, the cutting element having a cup-shaped surface and a cutting edge, the cup-shaped surface being configured to re-direct tissue cut by the cutting edge in a distal direction when the cup-shaped surface moves in the distal direction; and a raised element extending outwardly from the cup-shaped surface of the cutting element, the raised element being configured to direct cut particles of material towards one of more of the axis of rotation of the cutting element, a catheter longitudinal axis, or the tissue collection chamber; placing the catheter in the body lumen; and moving the catheter in the body lumen to contact the cutting element with the material in the body lumen.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; and a cutting element coupled to the rotatable shaft for rotating the cutting element about an axis of rotation, the cutting element having a cutting edge, and the cutting element being configured to oscillate in a direction substantially parallel to the axis of rotation of the cutting element; placing the catheter in the body lumen; and moving the catheter in the body lumen to contact the cutting element with the material in the body lumen. In one embodiment, the catheter is moved in a distal direction to contact the cutting edge with the material in the body lumen.

These and other aspects of the invention will become apparent from the following description of the preferred embodiments, drawings and claims. The details of one or more embodiments of the invention are set forth in the accompanying drawings and in the description below. Other features, objects, and advantages of the invention will be apparent from the description and drawings, and from the claims.

BRIEF DESCRIPTION OF THE DRAWINGS

FIG. 8 shows an isometric view of the embodiment of the cutting element illustrated in FIG. 7.

FIG. 8A shows an isometric view of one of the raised elements of the cutting element embodiment illustrated in FIG. 8.

FIG. 10 shows an isometric view of the embodiment of the cutting element illustrated in FIG. 9.

FIG. 10A shows an isometric view of one of the raised elements of the cutting element embodiment illustrated in FIG. 10.

FIG. 11 shows an isometric view of a modified version of the embodiment of the cutting element illustrated in FIG. 8.

FIG. 11A shows an isometric view of one of the raised elements of the cutting element embodiment illustrated in FIG. 11.

DETAILED DESCRIPTION

Figure 1:
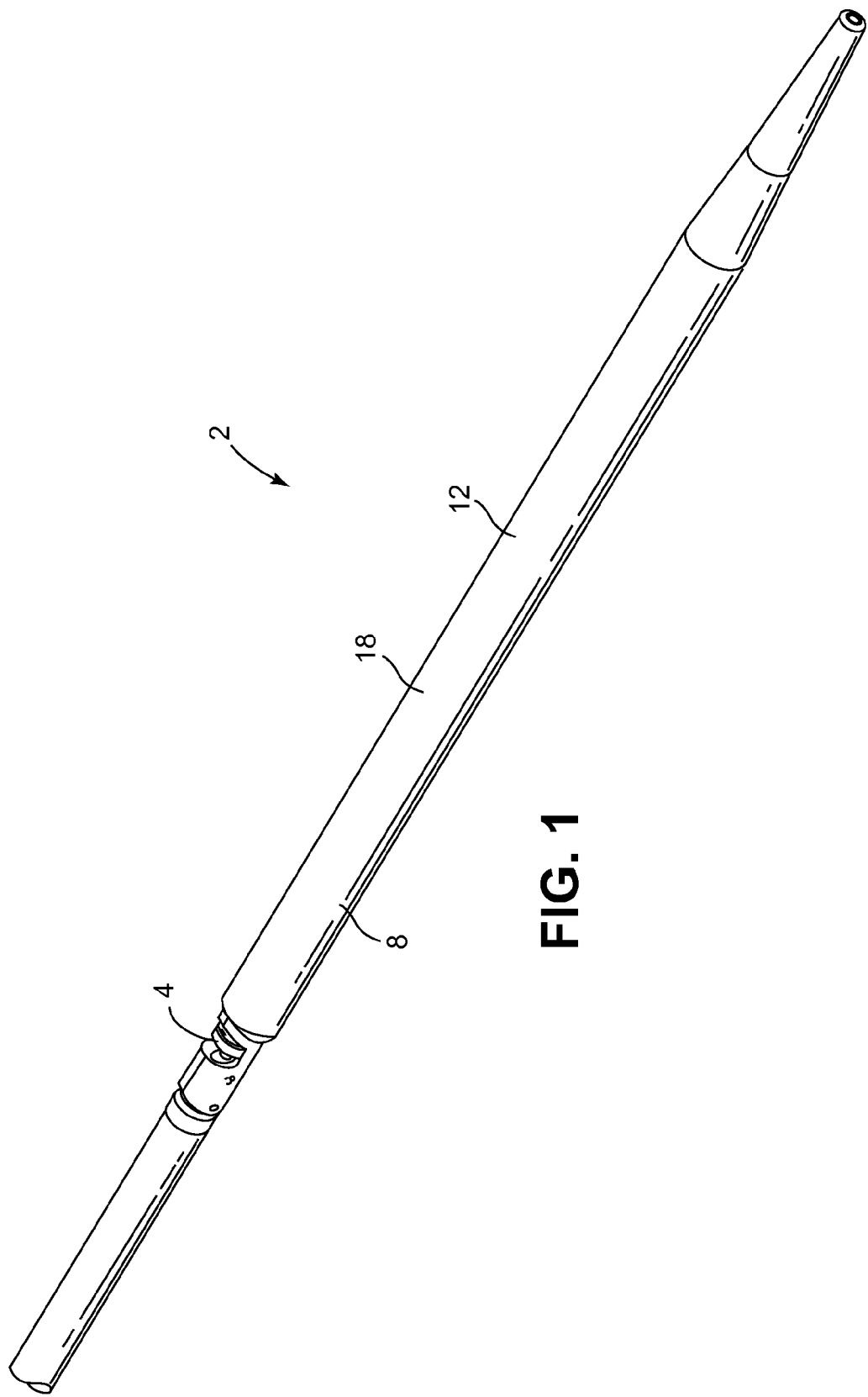
FIG. 1 shows an isometric view of a distal end of an atherectomy catheter.

The invention provides an atherectomy catheter comprising: a body having an opening; a rotatable shaft coupled to the body; a tissue collection chamber coupled to the body and positioned distal to the cutting element; a cutting element coupled to the rotatable shaft for rotating the cutting element about an axis of rotation, the cutting element having a cup-shaped surface and a cutting edge, the cup-shaped surface being configured to re-direct tissue cut by the cutting edge in a distal direction when the cup-shaped surface moves in the distal direction; and a raised element extending outwardly from the cup-shaped surface of the cutting element, the raised element being configured to direct cut particles of material towards one of more of the axis of rotation of the cutting element, a catheter longitudinal axis, or the tissue collection chamber. In an embodiment, the raised element is configured to direct cut particles of material towards the axis of rotation of the cutting element. In one embodiment, the cutting edge is at a radially outer edge of the cutting element. In an embodiment, the raised element comprises a curved raised element cutting edge. In an embodiment, the raised element comprises a first wall that extends from the curved raised element cutting edge to the cup-shaped surface, the first wall directing the cut particles of material towards the axis of rotation of the cutting element.

In an embodiment, the first wall curves from a relatively tangential angle with the cutting edge at the radially outer edge of the cutting element to a relatively radial angle closer to the axis of rotation of the cutting element. In one embodiment, the raised element comprises a distal wall that extends from the first, curved raised element cutting edge to a second edge, the distal wall forming an angle of less than 90 degrees with respect to the axis of rotation of the cutting element. In an embodiment, the first, curved raised element cutting edge is more distal than the second edge. In one embodiment, the minimum radial distance between the first, curved raised element cutting edge and the cutting edge of the cutting element is less than the minimum radial distance between the second edge and the cutting edge of the cutting element. In one embodiment, wherein an included angle between the first wall and the distal wall is an obtuse angle.

In one embodiment, the raised element is recessed proximally from the cutting edge by a longitudinal distance. For example, the raised element can be recessed proximally from the cutting edge by a longitudinal distance of 0.0010 to 0.0050 inch (0.0025 to 0.0127 cm). In an embodiment, the raised element is recessed from the cutting edge by a radial distance of 0.0010 to 0.0050 inch (0.0025 to 0.0127 cm).

In one embodiment, the raised element comprises a first wall that extends from a raised element cutting edge to the cup-shaped surface, the first wall directing the cut particles of material towards the axis of rotation of the cutting element and wherein the first wall forms an acute angle with the cup-shaped surface to form an undercut. In an embodiment, the raised element comprises a distal wall that extends from the first raised element cutting edge to a second edge, the distal wall forming an angle of less than 90 degrees with respect to the axis of rotation of the cutting element. In one embodiment, the first raised element cutting edge is more distal than the second edge. In an embodiment, the minimum radial distance between the first raised element cutting edge and the cutting edge of the cutting element is less than the minimum radial distance between the second edge and the cutting edge of the cutting element. In an embodiment, a wall having a rake angle is interspersed between the intersection of the first wall and the distal wall. In one embodiment, the rake angle is negative.

In an embodiment, the cup-shaped surface of the cutting element is smooth and uninterrupted throughout at least 300 degrees when viewed along the axis of rotation of the cutting element. In one embodiment, the cup-shaped surface of the cutting element is smooth and uninterrupted for at least 90% of the surface area of the cutting element when viewed along the axis of rotation of the cutting element. In an embodiment, the cup-shaped surface of the cutting element has an outer radius when viewed along the axis of rotation of the cutting element, the cup-shaped surface being continuous and uninterrupted from the axis of rotation to at least half the distance to the outer radius. In one embodiment, the atherectomy catheter further comprises a plurality of raised elements, the plurality of raised elements altogether occupying an area less than 60 degrees and less than 5% of the surface area when viewed along the axis of rotation of the cutting element, and the cup-shaped surface being smooth and uninterrupted for at least 90% of the surface area. In one embodiment, the atherectomy catheter comprises a plurality of raised elements extending outwardly from the cup-shaped surface, the plurality of raised elements being 1, 2, 3, 4, 6, or 8 raised elements.

In one embodiment, the cutting element is movable between a stored position and a cutting position relative to the opening. In an embodiment, the cutting element is moved between the stored position and the cutting position by sliding the cutting element against a cam surface. In an embodiment, a distal portion of the catheter relative to a proximal portion is deflected by sliding the cutting element against the cam surface. In an embodiment, the cutting element is configured to oscillate in a direction substantially parallel to the axis of rotation of the cutting element.

The invention provides an atherectomy catheter comprising: a body having an opening; a rotatable shaft coupled to the body; a tissue collection chamber coupled to the body and positioned distal to the cutting element; and a cutting element coupled to the rotatable shaft for rotating the cutting element about an axis of rotation, the cutting element having a cutting edge, and the cutting element being configured to oscillate in a direction substantially parallel to the axis of rotation of the cutting element. In one embodiment, the atherectomy catheter comprises a ramp having one or more recesses, the cutting element comprises one or more raised portions on a cam surface of the cutting element, the one or more raised portions fitting within the one or more recesses when the raised portions and the recesses are aligned, and the raised portions leaving and entering the recesses as the cutting element is rotated and thereby causing the cutting element to oscillate. In one embodiment, the atherectomy catheter comprises a ramp having one or more raised portions, the cutting element comprises one or more recesses on a cam surface of the cutting element, the one or more raised portions fitting within the one or more recesses when the raised portions and the recesses are aligned, and the raised portions leaving and entering the recesses as the cutting element is rotated and thereby causing the cutting element to oscillate. In one embodiment, the atherectomy catheter comprises a ramp having one or more raised portions, the cutting element comprises one or more raised portions on a cam surface of the cutting element, and the raised portions causing the cutting element to oscillate as the cutting element is rotated.

In one embodiment, the cutting element has a cup-shaped surface, the cup-shaped surface being configured to re-direct tissue cut by the cutting edge in a distal direction when the cup-shaped surface moves in the distal direction. In an embodiment, the cutting edge is a radially outer edge of the cutting element. In an embodiment, the catheter comprises a raised element extending outwardly from the cup-shaped surface of the cutting element. In an embodiment, the cutting edge is a radially outer edge of the cutting element, and the raised element is recessed proximally from the cutting edge when viewed along the axis of rotation of the cutting element. In one embodiment, the cutting element is movable between a stored position and a cutting position relative to the opening. In one embodiment, the cutting element is moved between the stored position and the cutting position by sliding the cutting element against a cam surface. In one embodiment, a distal portion of the catheter relative to a proximal portion is deflected by sliding the cutting element against the cam surface.

The invention provides a method of removing material from a body lumen, the method comprising providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft for rotating the cutting element about an axis of rotation, the cutting element having a cup-shaped surface and a cutting edge, the cup-shaped surface being configured to re-direct tissue cut by the cutting edge in a distal direction when the cup-shaped surface moves in the distal direction; and a raised element extending outwardly from the cup-shaped surface of the cutting element, the raised element being configured to direct cut particles of material towards one of more of the axis of rotation of the cutting element, a catheter longitudinal axis, or the tissue collection chamber; placing the catheter in the body lumen; and moving the catheter in the body lumen to contact the cutting element with the material in the body lumen. In one embodiment, the catheter is moved in a distal direction to contact the cutting edge with the material in the body lumen. In one embodiment, the catheter is placed in the body lumen with the cutting element in the stored position and the catheter is moved to contact the material with the cutting element in a cutting position. In one embodiment, the body lumen is a blood vessel.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; and a cutting element coupled to the rotatable shaft for rotating the cutting element about an axis of rotation, the cutting element having a cutting edge, and the cutting element being configured to oscillate in a direction substantially parallel to the axis of rotation of the cutting element; placing the catheter in the body lumen; and moving the catheter in the body lumen to contact the cutting element with the material in the body lumen. In one embodiment, the catheter is moved in a distal direction to contact the cutting edge with the material in the body lumen. In an embodiment, the catheter is placed in the body lumen with the cutting element in the stored position and the catheter is moved to contact the material with the cutting element in a cutting position. In an embodiment, the body lumen is a blood vessel.

The present invention provides an atherectomy catheter which has a cutting element that is able to cut both soft tissue and hard tissue. The cutting element has a sharp cutting edge that surrounds a cup-shaped surface. The cup-shaped surface directs the material which has been cut into a tissue chamber. The circumferential cutting edge and the cup-shaped surface together are well suited to cut and remove relatively soft tissue.

In one aspect of the invention, an atherectomy catheter is provided which has one or more raised elements extending from the cup-shaped surface. The raised element may be recessed longitudinally and radially from the outer cutting edge by a controlled distance such as 0.0010-0.0020 inch (0.0025 to 0.0051 cm) but may in other embodiments be closer or further from the outer cutting edge depending upon the application. The raised elements help to break up hard tissue such as calcified plaque. The raised elements are somewhat recessed from the distal end so that the cutting edge remains exposed to cut soft tissue. When the cutting element encounters tissue which is too hard to be cut sufficiently by the cutting edge, the raised elements help to break the harder tissue with a more blunt application of force.

In another aspect of the invention, the raised element is somewhat small so that a relatively large portion of the cup-shaped surface is smooth and uninterrupted. In this manner, the ability of the cutting element to direct tissue into the tissue chamber with the cup-shaped surface is not overly inhibited by the raised elements. For example, the raised elements may occupy an area less than 60 degrees when viewed along the longitudinal axis. Stated another way, the cup-shaped surface of the cutting element is smooth and uninterrupted throughout at least 300 degrees when viewed along the longitudinal axis. Stated still another way, the cup-shaped surface may be smooth and uninterrupted for at least 95% of the surface area of the cutting element when viewed along the longitudinal axis.

In yet another aspect of the invention, the raised element has a surface that tends to direct cut particles of material towards one or more of the axis of rotation of the cutter, the catheter axis, or a particle collection chamber.

In further aspects of the invention, the cutter oscillates in a direction roughly parallel to the axis of the cutter so as to impart a force on cut particles of material that directs them in a distal direction, towards a collection chamber, or in both directions.

Referring to FIGS. 1 to 4, an atherectomy catheter 2 is shown which has a cutting element 4, which is used to cut material from a blood flow lumen. The cutting element 4 is movable between a stored position (FIG. 2) and a cutting position (FIG. 3) relative to an opening 6 in a body 8 of the catheter 2. The cutting element 8 moves outwardly relative to the opening 6 so that a portion of the element 4 extends outwardly from the body 8 through the opening 6. The cutting element 4 may be positioned relative to the body 8 and opening 6 so that less than 90 degrees of the cutting element 4 is exposed to cut tissue. Of course, more of the cutting element 4 may be exposed without departing from numerous aspects of the invention.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated. Cutter 4 preferably has a diameter slightly less than that of the maximum size of catheter 2, typically 0.010" (0.025 cm), 0.015" (0.038 cm), 0.020" (0.051 cm), 0.025" (0.064 cm) or 0.030" (0.076 cm) less. However these relative dimensions are not meant to be limiting.

The catheter 2 is moved distally through a vessel with the cutting element 4 in the working or cutting position as described in further detail below. As the catheter 2 moves through the blood vessel, the tissue is cut by the cutting element 4 and is directed into a tissue chamber 12 positioned distal to the cutting element 4. The tissue chamber 12 may be somewhat elongate to accommodate the tissue which has been cut.

The cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

The cutting element 4 is coupled to a shaft 20 that extends through a lumen 21 in the catheter 2. The cutting element 4 is rotated about a longitudinal axis LA when the shaft rotates. The cutting element 4 is rotated at about 1 to 160,000 rpm but may be rotated at any other suitable speed depending upon the particular application.

Figure 2:
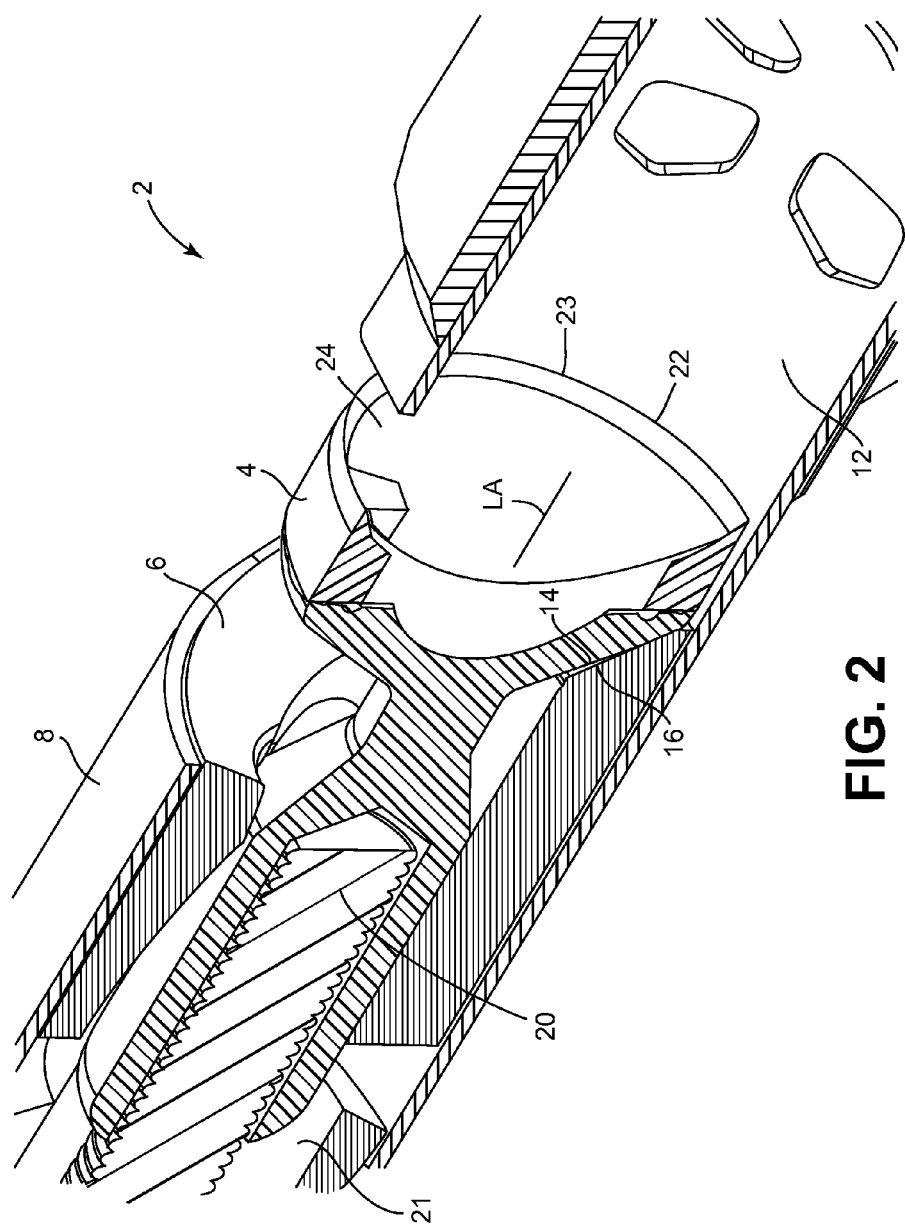
FIG. 2 is an isometric cross-sectional view of a portion of the atherectomy catheter of FIG. 1 with a cutting element in a stored position.
Figure 4:
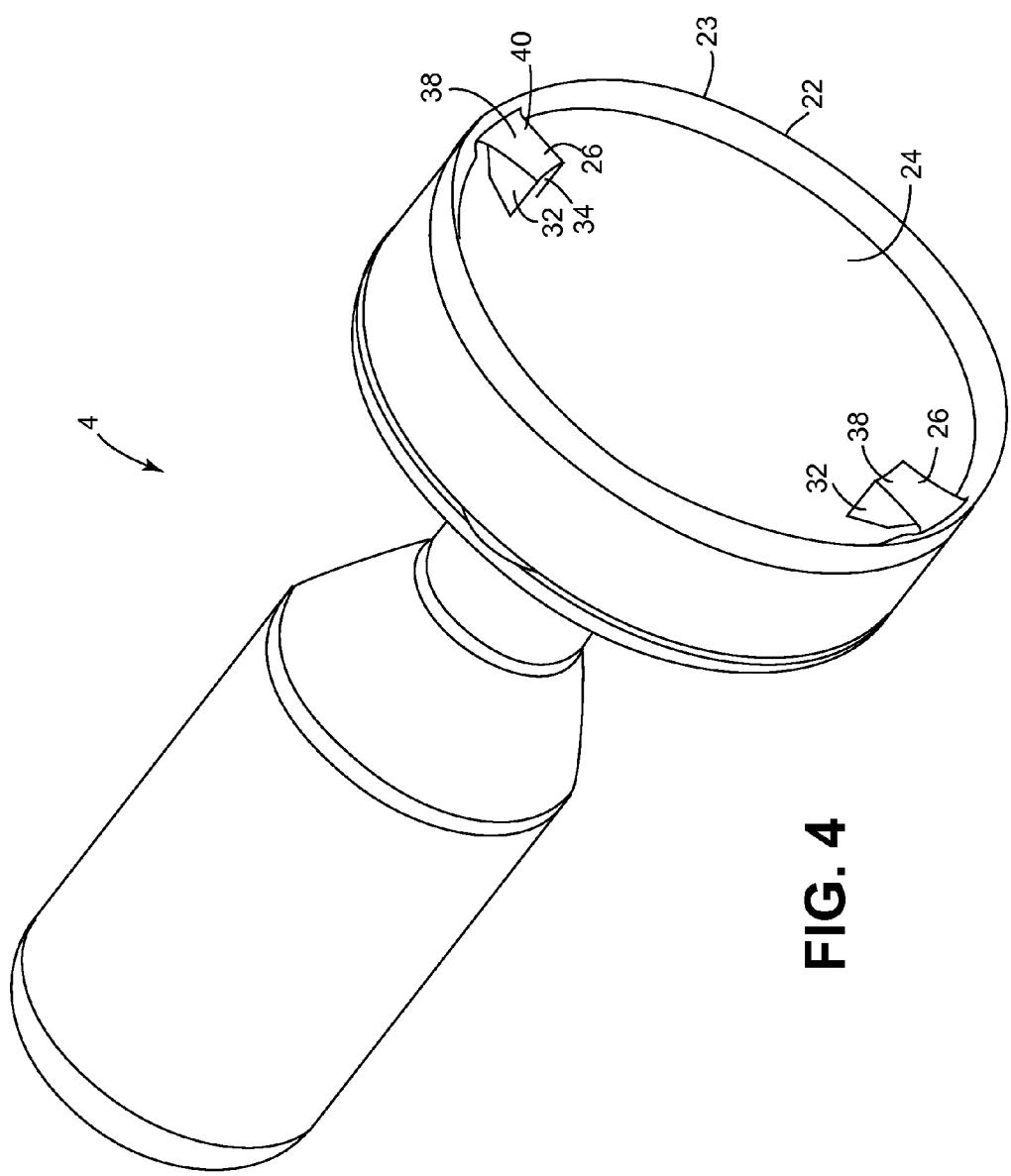
FIG. 4 shows an isometric view of an embodiment of a cutting element.
Figure 5:
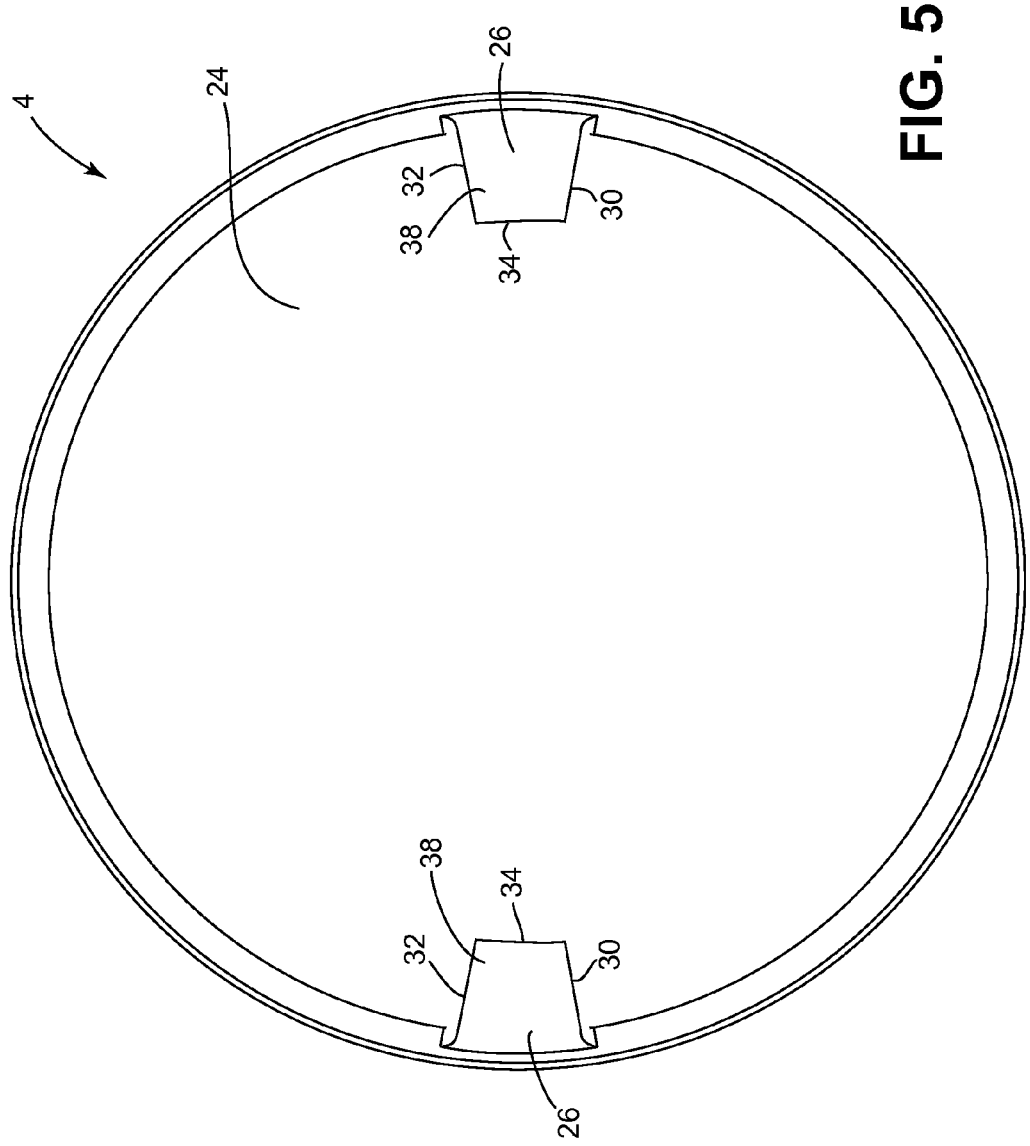
FIG. 5 shows an end view of an embodiment of a cutting element.

Referring to FIGS. 2, 4 and 5, the cutting element 4 is shown. The term "along the longitudinal axis" as used herein shall mean the view of FIG. 5 that shows the distal end of the cutting element 4 when viewed in the direction of the longitudinal axis and/or the axis of rotation. The cutting element 4 has a cutting edge 22 that may be a continuous, uninterrupted, circular-shaped edge although it may also include ridges, teeth, serrations or other features without departing from the scope of the invention. The cutting edge 22 may be at a radially outer edge 23 of the cutting element 4 when the cutting element 4 is in the cutting position.

The cutting element 4 has a cup-shaped surface 24, which directs the tissue cut by the cutting edge 22 into the tissue chamber 12. The cup-shaped surface 24 may be a smooth and continuous surface free of through-holes, teeth, fins or other features, which disrupt the smooth nature of the surface 24 for at least half the distance from the longitudinal axis LA to the outer radius at the cutting edge 22. The cup-shaped surface 24 may also be free of any such features throughout an area of at least 300 degrees relative to the longitudinal axis LA.

Cutter 4 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 6:
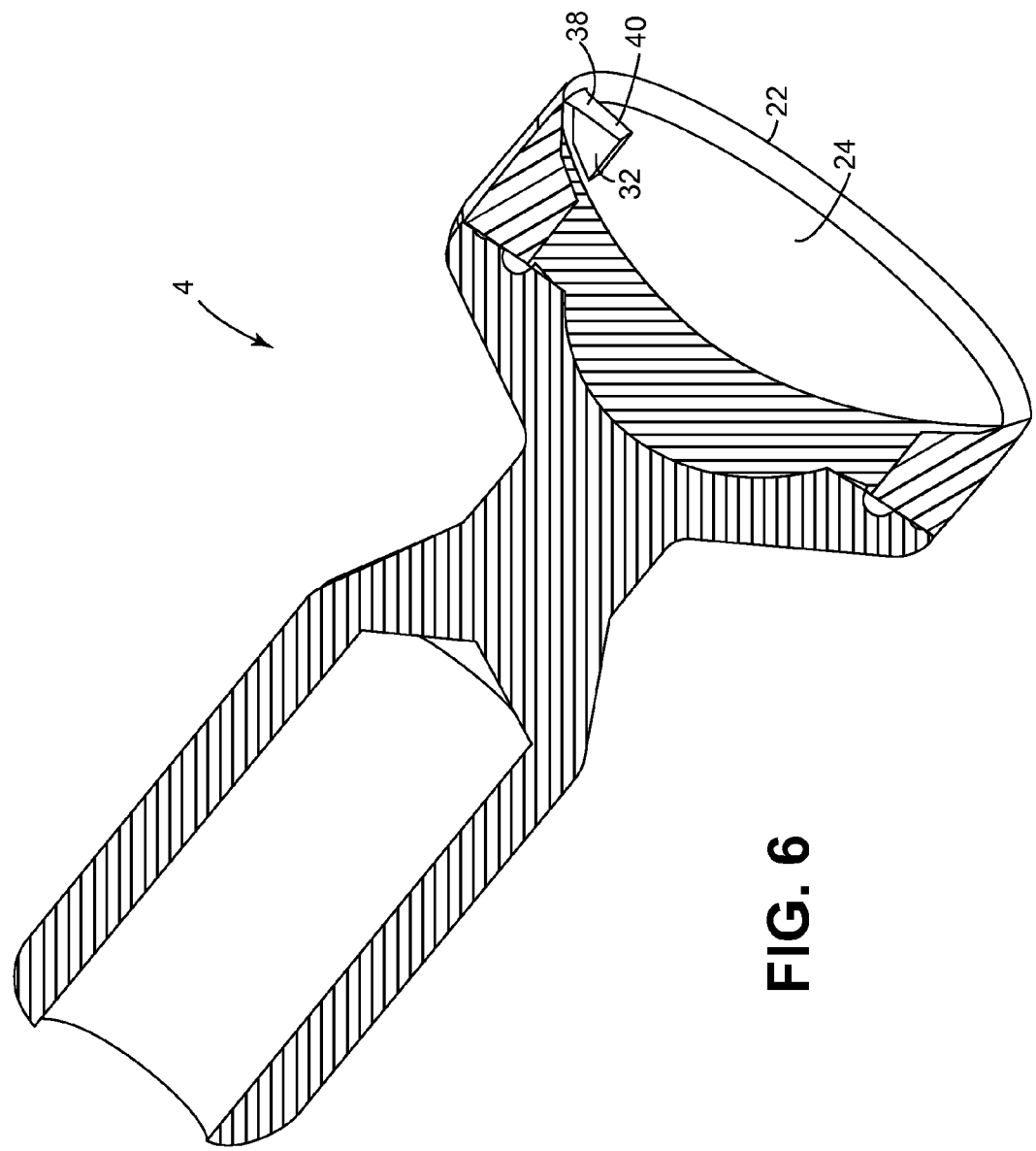
FIG. 6 is an isometric cross-sectional view of an embodiment of a cutting element.

Referring to FIGS. 4 to 6, one or more raised elements 26 extend outwardly from the cup-shaped surface 24 with FIG. 5 showing two raised elements 26. The raised element 26 is a small wedge of material that rises relatively abruptly from the cup-shaped surface 24. The raised element 26 has a first wall 30 and a second wall 32 that both extend radially and form an angle of about 20 degrees therebetween so that the two raised elements 26 together occupy an area of about 40 degrees and altogether may be less than 60 degrees. A third wall 34 extends between the radially inner portion of the first and second walls 30, 32. The raised element 26 helps to break up hard tissue and plaque by applying a relatively blunt force to the hard tissue or plaque since cutting such tissue with the cutting edge 22 is often not effective.

The raised elements 26 altogether occupy a relatively small part of the cup-shaped surface 24. The raised elements 26 together may occupy less than 5% of a surface area of the cutting element 4. The term "surface area of the cutting element" as used herein shall mean the surface area which is radially inward from the outer or cutting edge 22 and is exposed when viewed along the longitudinal axis LA. Stated another way, at least 95% of the surface area of the cutting element is a smooth cup-shaped surface when viewed along the longitudinal axis. By sizing and positioning the raised element 26 in this manner, the raised element 26 does not interfere with the ability of the cutting element 4 to cut and re-direct tissue into the tissue chamber while still providing the ability to break up hard tissue and plaque with the raised element 26.

The raised element 26 may be recessed from the cutting edge 22 longitudinally and/or radially. The raised element 26 may be recessed longitudinally (along axis LA) from the cutting edge 0.0010 to 0.0020 inch (0.0025 to 0.0051 cm) and may be recessed about 0.0015 inch (0.0038 cm). The raised element 26 may be recessed radially from the cutting edge 22 by about the same amount. A distal wall 38 of the cutting element 4 forms a flat surface 40, which is perpendicular to the longitudinal axis LA so that the entire surface is recessed the same distance from the cutting edge. The distal wall 38 may take any other shape, such as a curved shape, or may be tilted, inclined or beveled as now described.

Figure 7:
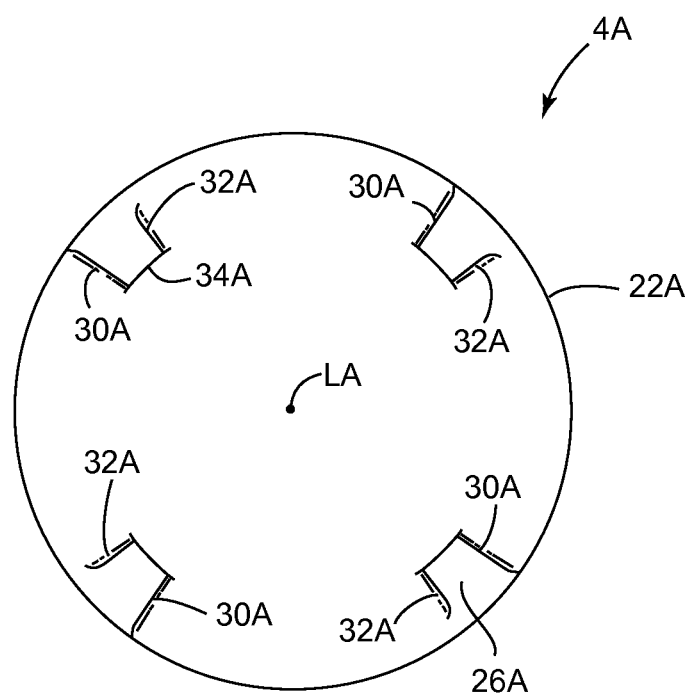
FIG. 7 shows an end view of another embodiment of a cutting element, which may be used with the atherectomy catheter shown in FIG. 1.

Referring to FIGS. 7, 8 and 8A, another cutting element 4A is shown wherein the same or similar reference numbers refer to the same or similar structure and all discussion concerning the same or similar features of the cutting element 4 are equally applicable here unless noted otherwise. The cutting element 4A has a cutting edge 22A that may be a continuous, uninterrupted, circular-shaped edge although it may also include ridges, teeth, serrations or other features without departing from the scope of the invention. The cutting edge 22A may be at a radially outer edge 23A of the cutting element 4A when the cutting element 4A is in the cutting position. The cutting element 4A has a cup-shaped surface 24A that directs the tissue cut by the cutting edge 22A into the tissue chamber 12 (see FIG. 2). The cup-shaped surface 24A may be a substantially smooth and continuous surface as described above in connection with the cutting element 4.

One or more raised elements 26A extend outwardly from the cup-shaped surface 24A. FIG. 8 shows four raised elements 26A but may include any number such as 1, 2, 3, 4, 6 or 8 raised elements. The raised element 26A is a small wedge of material that rises relatively abruptly from the cup-shaped surface 24A. The raised element 26A has a first wall 30A and a second wall 32A which, in one embodiment, both extend radially and form an angle of about 1 to 30 degrees therebetween so that the four raised elements 26A together occupy an area of about 4 to 60 degrees and altogether may be less than 60 degrees. A third wall 34A extends between the radially inner portion of the first and second walls 30A, 32A. In some embodiments the raised elements 26A may occupy a relatively small part of the cup-shaped surface 24A and may be recessed from the cutting edge 22A in the manner described above in connection with the cutting element 4. In other embodiments at least 60%, 70%, 80% or 90% of the surface area of the cutting element is a smooth cup-shaped surface.

A distal wall 38A of the cutting element 4A has a surface 40A that forms an angle of about 30 to 90 degrees with respect to the longitudinal axis LA. The entire surface 40A may still be somewhat close to but recessed from the cutting edge 22A so that the entire surface 40A is at least 0.0010, 0.0020, 0.0030, 0.0040 or 0.0050 inches (0.0025, 0.0051, 0.0076, 0.0101, or 0.0127 cm) from the cutting edge. An edge 50 formed at the intersection of wall 30A and distal wall 38A is closer to the cutting edge 22A than an edge 52 formed at the intersection of wall 32A and distal wall 38A. The cutting element 4A may be rotated in either direction so that the raised edge 50 may be the leading or trailing edge. In some embodiments the raised edge may be 0.0010 to 0.0020 inch (0.0025 to 0.0051 cm) from the cutting edge. The raised elements 26A may all be formed in the same manner or may be different from one another. For example, some of the elements 26A could be angled in different directions so that two of the elements have the raised edge 50 as the leading edge and two of the elements 26A have the raised edge 50 as the trailing edge. The raised elements 26A may also subtend different angles, be of different heights or may have different radial lengths without departing from various aspects of the present invention.

Figure 9:
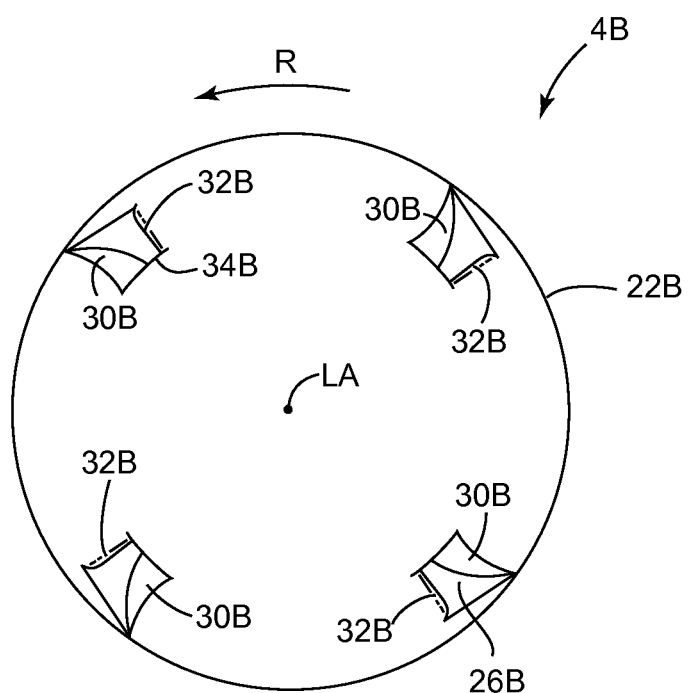
FIG. 9 shows an end view of another embodiment of a cutting element, which may be used with the atherectomy catheter shown in FIG. 1.

Referring to FIGS. 9, 10 and 10A, another cutting element 4B is shown wherein the same or similar reference numbers refer to the same or similar structure and all discussion concerning the same or similar features of the cutting element 4 are equally applicable here unless noted otherwise. The cutting element 4B has a cutting edge 22B that may be a continuous, uninterrupted, circular-shaped edge although it may also include ridges, teeth, serrations or other features without departing from the scope of the invention. The cutting edge 22B may be at a radially outer edge 23B of the cutting element 4B when the cutting element 4B is in the cutting position. The cutting element 4B has a cup-shaped surface 24B that directs the tissue cut by the cutting edge 22B into the tissue chamber 12 (see FIG. 2). In one embodiment the cup-shaped surface 24B may be a substantially smooth and continuous surface as described above in connection with the cutting element 4.

One or more raised elements 26B, extend outwardly from the cup-shaped surface 24B. FIGS. 9 and 10 show four raised elements 26B but may include any number such as 1, 2, 3, 4, 6 or 8 raised elements. The raised element 26B is a small wedge of material that rises relatively abruptly from the cup-shaped surface 24B and which subtends an arc of about 1 to 30 degrees relative to axis LA, the four raised elements 26B subtending an arc of about 4 to 60 degrees altogether. The raised element 26B has a first wall 30B that extends between a curved cutting edge 50B and cup shaped surface 24B and also has a second wall 32B which extends radially relative to axis LA. A third wall 34B extends between the radially inner portion of the first and second walls 30B, 32B. In some embodiments the raised elements 26B may occupy a relative small part of the cup-shaped surface 24B and may be recessed from the cutting edge 22B in the manner described above in connection with the cutting element 4. In other embodiments at least 60%, 70%, 80% or 90% of the surface area of the cutting element is a smooth cup-shaped surface.

A distal wall 38B of the cutting element 4B has a surface 40B that forms an angle of less than 90 degrees with respect to the longitudinal axis LA. In some embodiments the surface 40B is angled such that edge 50B is more distal than edge 52B. The entire surface 40B may still be somewhat close to but recessed from the cutting edge 22B so that the entire surface 40B is from 0.0010 to 0.0050 inch (0.0025 to 0.0127 cm), including 0.0010, 0.0020, 0.0030, 0.0040 or 0.0050 inch (0.0025, 0.0051, 0.0076, 0.0101, or 0.0127 cm), from the cutting edge. An edge 50B formed at the intersection of wall 30B and distal wall 38B is closer to the cutting edge 22B than an edge 52B formed at the intersection of wall 32B and distal wall 38B. The included angle between wall 30B and surface 40B, in the vicinity of edge 50B, is greater than 90 degrees. The cutting element 4B may be rotated in either direction so that the raised edge 50B may be the leading or trailing edge. In one embodiment, the cutter 4B is rotated in the direction of arrow R so that edge 50B is the leading edge. Raised edges 50B, 52B may be 0.0010 to 0.0020 inch (0.0025 to 0.0051 cm) from the cutting edge. The raised elements 26B may all be formed in the same manner or may be different from one another. For example, some of the elements 26B could be angled in different directions so that two of the elements have the raised edge 50B as the leading edge and two of the elements 26A have the raised edge 50B as the trailing edge. The raised elements 26B may also subtend different angles, be of different heights or may have different radial lengths without departing from various aspects of the present invention.

In one embodiment cutter 4B is rotated in the direction of arrow R and pushed distally to force cup shaped surface 24B and raised elements 26B into contact with material such as atheroma or plaque. Raised elements 26B will tend to concentrate cutting force along edge 50B due to relief angle between cutter axis LA and surface 40B. Cutter 4B will tend to scrape away material such as atheroma or plaque rather than cut into this material due to the obtuse included angle between wall 30B and surface 40B, in the vicinity of edge 50B. Material contacted by raised elements 26B will tend to be directed towards axis LA by surface 30B which curves from a relatively tangential angle near edge 22B to a relatively radial angle near edge 34B.

Referring to FIGS. 11 and 11A, another cutting element 4C is shown. Cutting element 4C is a modified version of cutting element 4A. The modification consists of adding an undercut 41C to the leading face of one or more raised element 26A, resulting in modified raised element 26C. When cutter 4C is rotated in the direction of arrow T the undercut directs particles of material into the concave cavity defined by cup shaped surface 24A of the cutter, and towards axis LA of the cutter. Optionally an undercut can be applied to the leading face of one or more raised element 26, 26B of cutting elements 4, 4B respectively as well as to one or more raised elements 26A of cutting element 4A.

Undercut 41C is defined by wall 30C which is oriented at an acute angle to surface 40A, which intersects cup shaped surface 24A, and which meets wall 34A. The plane of wall 30C also intersects axis LA at less than 5, 10, 15, or 20 degrees such that, when cutter 4C is spinning in direction T, particles of material tend to travel along wall 30C in directions away from cutting edge 22A and towards axis LA. In some embodiments wall 43C may be interspersed between the intersection of wall 30C and wall 40A. Wall 43C may be oriented at any desired rake angle, such as for example a negative rake angle where the raised element will tend to not dig in to material being cut.

Use of the catheter 2 is now described in connection with the cutting element 4 but is equally applicable to use of the catheter 2 with either the cutting element 4A, the cutting element 4B, or the cutting element 4C. The catheter 2 is introduced into the patient in a conventional manner using a guidewire (not shown) or the like. The catheter 2 is advanced with the cutting element in the stored position of FIG. 2 until the catheter is positioned proximal to the location where material is to be removed. The cutting element 4 is then moved proximally so that the ramp 16 and cam surface 14 engage to move the cutting element 4 to the cutting position of FIG. 3 and to deflect the tip of the catheter 2 to move the cutting element 4 toward the tissue to be cut. The cutting element 4 is rotated about longitudinal axis LA and catheter 2 is then moved distally through the vessel so that the cutting element 4 cuts tissue. The tissue, which has been cut, is directed into the tissue chamber 12 by the cup shaped surface 24, one or more raised elements 26, by curved surface 30B (of cutting element 4B), or by any combination of a cup shaped surface, raised element, or curved surface.

More specifically, when using cutting element 4B and rotating the cutting element in the direction of arrow R (FIG. 9) cutting edge 22B slices softer material and cup shaped surface directs the cut material into tissue chamber 12; the relief angle assures that distally directed force on the catheter is concentrated at raised element edge 50B rather than distributed over surface 40B; raised elements 26B will tend to scrape away or pulverize harder material such as calcium due to the obtuse included angle between wall 30B and surface 40B in the vicinity of edge 50B; curved surface 30B directs material particles towards cutter axis LA; and curved surface 30B when rotating creates a fluid vortex that tends to direct material particles towards cutter axis LA and distally into tissue chamber 12.

More specifically, when using an undercut such as that shown for cutting element 4C and rotating the cutting element in the direction of arrow T (FIG. 11) undercut 41C directs material away from cutting edge 22A, along cup shaped surface towards axis LA, and radially towards axis LA of the cutting element.

Figure 12:
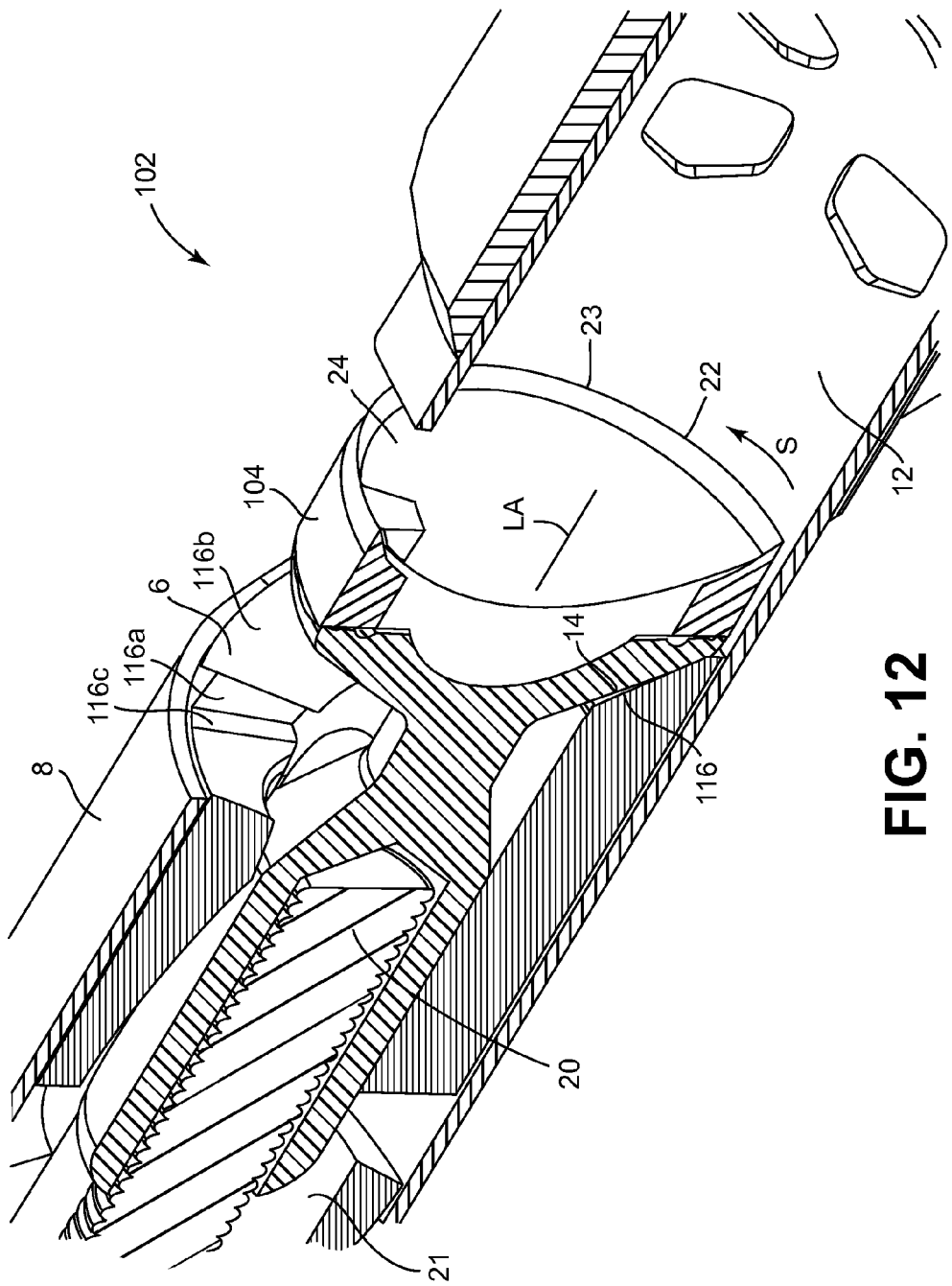
FIG. 12 illustrates an isometric cross-sectional view of a portion of an atherectomy catheter having a cutting element that oscillates in a direction generally along the axis of the cutting element.
Figure 13:
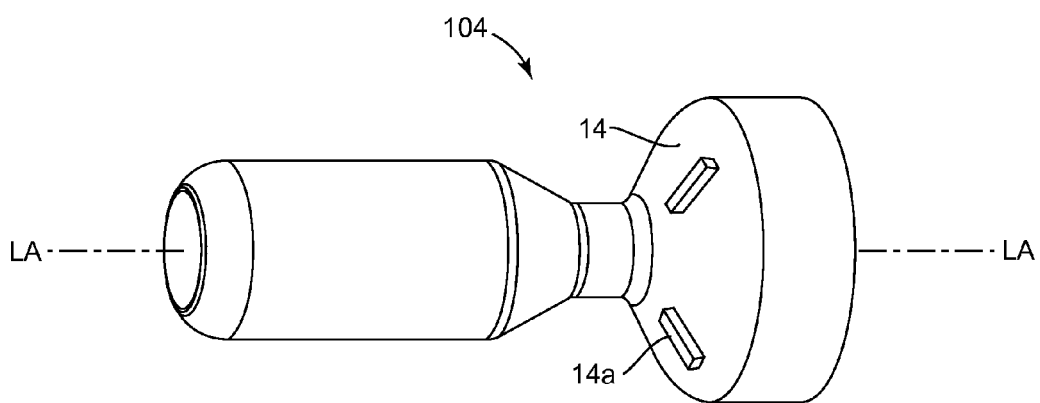
FIG. 13 illustrates an isometric view of a component of the catheter shown in FIG. 12.

In another embodiment, FIGS. 12 and 13 show atherectomy catheter 102 having a cutting element 104 that oscillates in a direction generally along axis LA of the cutting element. Atherectomy catheter 102 is similar to atherectomy catheter 2 wherein the same or similar reference numbers refer to the same or similar structure and all discussion concerning the same or similar features of the atherectomy catheter 2 are equally applicable here unless noted otherwise.

Atherectomy catheter 102 is comprised of ramp 116 and cutter 104. The cutting element 104 is moved proximally from the stored position (FIG. 12) so that a cam surface 14 on the cutting element 104 engages a ramp 116 on the body 8 of the catheter 102. The interaction between the cam surface 14 and the ramp 116 causes the cutting element 104 to move to the cutting position (FIG. 3) and also causes a tip 18 to deflect which tends to move the cutting element 104 toward the tissue to be cut.

Cutter 104 is comprised of one or more raised portions 14a on cam surface 14; also ramp 116 is comprised of one or more recesses 116a in ramp surface 116b. Recesses and raised portions are relatively dimensioned such that raised portion 14a can fit within recess 116a. Recess 116a is also comprised of at least one edge 116c. Cam surface 14 of cutting element 104 is preloaded into pressured contact against ramp 116. In one embodiment catheter 102 is assembled with shaft 20 in tension and catheter body 8 in compression by means known in the art to provide such preload. In another embodiment catheter 102 is comprised of a spring (not shown) that forces raised portion 14a against ramp surface 116b. Cutter 104 is comprised of cup shaped surface 24 and cutting edge 22 and may be comprised of zero, 1, 2, 3, 4, 6, or 8 raised elements in any mixture or combination of raised elements 26, 26A, 26B, or 26C.

In an alternative embodiment (not shown) cutter 104 is comprised of one or more recesses in cam surface 14 and ramp 116 is comprised of one or more raised portions on ramp surface 116b. In yet another embodiment (not shown) cutter 104 is comprised of one or more raised portions on cam surface 14 and ramp 116 is comprised of one or more raised portions on ramp surface 116b.

Figure 3:
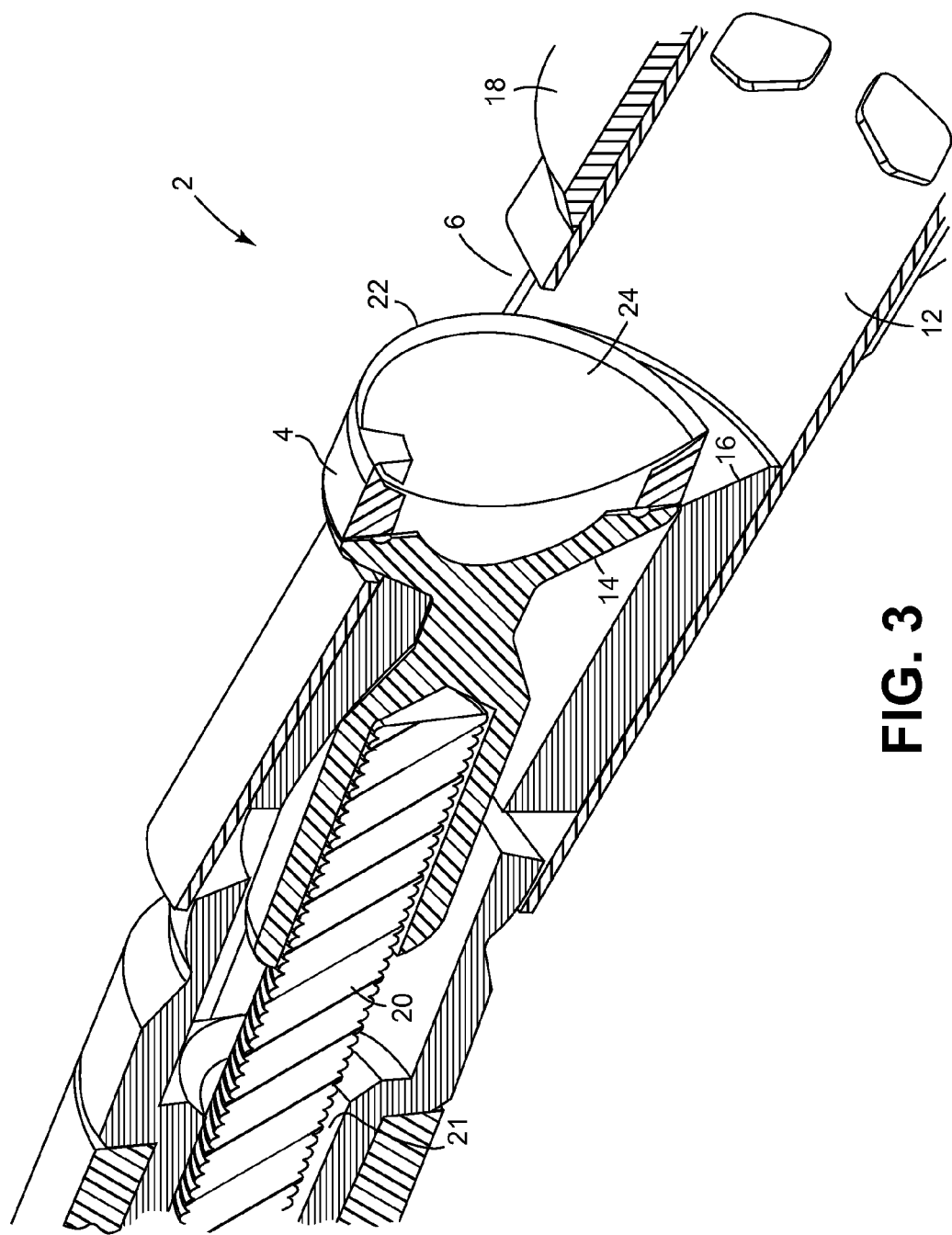
FIG. 3 is an isometric cross-sectional view of a portion of the atherectomy catheter of FIG. 1 with a cutting element in a working position.

In use catheter 102 is introduced into the patient in a conventional manner using a guidewire (not shown) or the like. The catheter 2 is advanced with the cutting element in the stored position of FIG. 12 until the catheter is positioned at the location where material is to be removed. The cutting element 104 is then moved proximally so that the ramp 116 and cam surface 14 engage to move the cutting element 104 to the cutting position and to deflect the tip of the catheter 2 to move the cutting element 104 toward the tissue to be cut (FIG. 3). The cutting element 104 is rotated about longitudinal axis LA and catheter 102 is then moved distally through the vessel so that the cutting element 104 cuts tissue. The tissue, which has been cut, is directed into the tissue chamber 12 by cup shaped surface 24. While the cutting element 104 is rotated about longitudinal axis LA (in, for example, the direction of arrow S) raised portions 14a will slide along surface 116b of ramp 116 until the preload of cutter 104 against ramp 116 causes raised portion 14a to enter into recess 116a of ramp 116. Further rotation of cutting element 104 causes raised portion 14a to contact recess edge 116c and be ejected from recess 116a of ramp 116 thereby producing a hammer-like impact of cutter 104 against the material to be removed. In the case where the material to be removed has brittle characteristics, the material will be crushed into smaller particles thereby facilitating its removal. Repeated rotation of cutter 104 will produce repeated hammer-like blows of the cutter 104 against the material to be removed. The oscillations in a direction roughly parallel to the axis of the cutting element impart a force on cut particles of material that directs them in a distal direction, towards a collection chamber, or in both directions.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. An atherectomy catheter comprising:
 a body having an opening;
 a rotatable shaft coupled to the body;
 a cutting element coupled to the rotatable shaft for rotating the cutting element about an axis of rotation, the cutting element having a cup-shaped surface and a cutting edge, the cup-shaped surface being configured to re-direct tissue cut by the cutting edge in a distal direction when the cup-shaped surface moves in the distal direction;
 a tissue collection chamber coupled to the body and positioned distal to the cutting element; and
 a raised element comprising first, second and third walls extending outwardly and distally from the cup-shaped surface of the cutting element, the raised element having a distal wall extending between distal edges of the first, second and third walls, a curved raised element cutting edge being formed at an intersection of the distal wall and the first wall, the raised element being configured to direct cut particles of material towards one or more of the axis of rotation of the cutting element, a catheter longitudinal axis, or the tissue collection chamber.

2. The atherectomy catheter of claim 1, wherein the raised element is configured to direct cut particles of material towards the axis of rotation of the cutting element.

3. The atherectomy catheter of claim 2, wherein the cutting edge is at a radially outer edge of the cutting element.

4. The atherectomy catheter of claim 1, wherein the first wall curves from a relatively tangential angle with the cutting edge at a radially outer edge of the cutting element to a relatively radial angle closer to the axis of rotation of the cutting element.

5. The atherectomy catheter of claim 4, wherein the distal wall extends from the curved raised element cutting edge to a second edge, the distal wall forming an angle of less than 90 degrees with respect to the axis of rotation of the cutting element.

6. The atherectomy catheter of claim 5, wherein the curved raised element cutting edge is more distal than the second edge.

7. The atherectomy catheter of claim 6, wherein a minimum radial distance between the curved raised element cutting edge and the cutting edge of the cutting element is less than a minimum radial distance between the second edge and the cutting edge of the cutting element.

8. The atherectomy catheter of claim 5, wherein an included angle between the first wall and the distal wall is an obtuse angle.

9. The atherectomy catheter of claim 3, wherein the raised element is recessed proximally from the cutting edge by a longitudinal distance.

10. The atherectomy catheter of claim 9, wherein the raised element is recessed proximally from the cutting edge by a longitudinal distance of 0.0010 to 0.0050 inch (0.0025 to 0.0127 cm).

11. The atherectomy catheter of claim 3, wherein the raised element is recessed from the cutting edge by a radial distance of 0.0010 to 0.0050 inch (0.0025 to 0.0127 cm).

12. The atherectomy catheter of claim 2, wherein the first wall is shaped to direct the cut particles of material towards the axis of rotation of the cutting element and wherein the first wall forms an acute angle with the cup-shaped surface to form an undercut.

13. The atherectomy catheter of claim 12, wherein the distal wall extends from the raised element cutting edge to a second edge, the distal wall forming an angle of less than 90 degrees with respect to the axis of rotation of the cutting element.

14. The atherectomy catheter of claim 13, wherein the raised element cutting edge is more distal than the second edge.

15. The atherectomy catheter of claim 14, wherein a minimum radial distance between the raised element cutting edge and the cutting edge of the cutting element is less than a minimum radial distance between the second edge and the cutting edge of the cutting element.

16. The atherectomy catheter of claim 1, wherein the cup-shaped surface of the cutting element is smooth and uninterrupted throughout at least 300 degrees when viewed along the axis of rotation of the cutting element.

17. The atherectomy catheter of claim 1, wherein the cup-shaped surface of the cutting element is smooth and uninterrupted for at least 90% of the surface area of the cutting element when viewed along the axis of rotation of the cutting element.

18. The atherectomy catheter of claim 1, wherein the cup-shaped surface of the cutting element has an outer radius when viewed along the axis of rotation of the cutting element, the cup-shaped surface being continuous and uninterrupted from the axis of rotation to at least half the distance to the outer radius.

19. The atherectomy catheter of claim 1 wherein the cup-shaped surface of the cutting element has a surface area, further comprising a plurality of raised elements, the plurality of raised elements altogether occupying less than 5% of the surface area of the cup-shaped surface when viewed along the axis of rotation of the cutting element, and the cup-shaped surface being smooth and uninterrupted for at least 90% of the surface area.

20. The atherectomy catheter of claim 1, wherein a plurality of raised elements extend outwardly from the cup-shaped surface, the plurality of raised elements being 2, 3, 4, 6, or 8 raised elements.

21. The atherectomy catheter of claim 1, wherein the cutting element is movable between a stored position and a cutting position relative to the opening.

22. The atherectomy catheter of claim 21, wherein the cutting element is moved between the stored position and the cutting position by sliding the cutting element against a cam surface.

23. The atherectomy catheter of claim 22, wherein a distal portion of the catheter relative to a proximal portion is deflected by sliding the cutting element against the cam surface.

24. The atherectomy catheter of claim 1, wherein the cutting element is configured to oscillate in a direction substantially parallel to the axis of rotation of the cutting element.

* * * * *